United States Patent [19]

Page

[11] Patent Number: 4,597,904
[45] Date of Patent: Jul. 1, 1986

[54] PROCESS FOR THE PREPARATION OF α-6-DEOXY-TETRACYCLINES

[75] Inventor: Philip R. Page, Parede, Portugal

[73] Assignee: Hovione Inter Ltd., Switzerland

[21] Appl. No.: 641,607

[22] Filed: Aug. 17, 1984

[30] Foreign Application Priority Data

Aug. 17, 1983 [PT] Portugal .............................. 77210[U]
Mar. 29, 1984 [PT] Portugal .............................. 78334[U]

[51] Int. Cl.$^4$ .......................................... C07C 103/19
[52] U.S. Cl. .............................. 260/351.5; 260/351.1
[58] Field of Search ........................... 260/351.5, 351.1

[56] References Cited

U.S. PATENT DOCUMENTS

| | | | |
|---|---|---|---|
| 3,200,149 | 8/1965 | Blackwood et al. | 260/351.5 |
| 3,397,231 | 8/1968 | Korst | 260/559 |
| 3,442,943 | 5/1969 | Martell et al. | 260/351.5 |
| 3,444,198 | 5/1969 | Korst | 260/351.5 |
| 3,484,483 | 12/1969 | Korst | 260/351.5 |
| 3,795,707 | 3/1974 | Luciano | 260/559 AT |
| 3,849,491 | 11/1974 | Villax et al. | 260/351.5 |
| 3,907,890 | 9/1975 | Scanio | 260/351.5 |
| 3,954,862 | 5/1976 | Morris, Jr. | 260/351.5 |
| 3,962,331 | 6/1976 | Cotti | 260/351.5 |
| 4,001,321 | 1/1977 | Faubl | 260/351.5 |
| 4,061,676 | 12/1977 | Villax | 260/559 AT |
| 4,207,258 | 6/1980 | Broggi et al. | 260/351.5 |
| 4,500,458 | 2/1985 | Villax et al. | 260/351.5 |

FOREIGN PATENT DOCUMENTS

| | | | |
|---|---|---|---|
| 668581 | 8/1963 | Canada | 260/351.5 |
| 0072435 | 2/1983 | European Pat. Off. | |
| 86046 | 8/1983 | European Pat. Off. | 260/351.5 |
| 2216268 | 8/1974 | France | 260/351.5 |
| 32257 | 2/1982 | Japan | 260/351.5 |
| 1360006 | 7/1974 | United Kingdom | |

OTHER PUBLICATIONS

Chemical Abstracts, vol. 86, 1977, p. 89476f.
British Pharmacopoeia 1980, vol. I, pp. 168–169.

Primary Examiner—Glennon H. Hollrah
Assistant Examiner—Raymond Covington
Attorney, Agent, or Firm—Ostrolenk, Faber, Gerb & Soffen

[57] ABSTRACT

A process for the preparation of α-6-deoxy-tetracyclines by the stereoselective heterogeneous hydrogenation of a 6-demethyl-6-deoxy-6-methylene-tetracycline or an acid addition salt thereof, in the presence of a tertiary phosphine, or the simultaneous dehalogenation and stereo-selective heterogeneous hydrogenation of an 11a-halo-6-demethyl-6-deoxy-6-methylene-tetracycline or an acid addition salt thereof, in the presence of a tertiary phosphine, characterized by the use of a rhodium salt catalysts, wherein the rhodium is bonded to a polysiloxane carrier, having the following formulae:

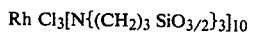

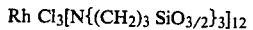

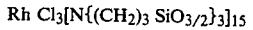

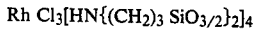

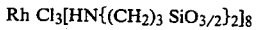

permitting easy recovery of the rhodium, by simple filtration.

13 Claims, No Drawings

PROCESS FOR THE PREPARATION OF α-6-DEOXY-TETRACYCLINES

The present refers to a new process for the preparation of α-6-deoxy-tetracyclines, which has the advantages of very high yields of practically pure products, plus the fact that it is considerably more economic than any of the prior art processes. More particularly, the present invention refers to the preparation of compounds of formula I

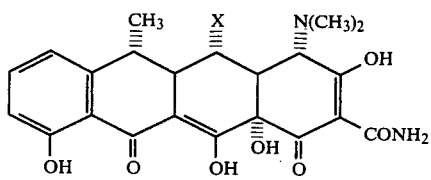

in which X is hydrogen or a hydroxyl group, from the corresponding 6-methylene tetracycline or 11a-halo analogue of formulae II and III, respectively

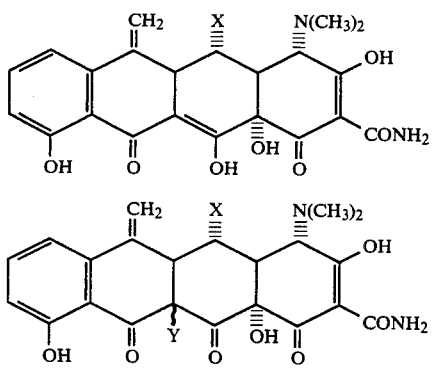

wherein X is hydrogen or a hydroxyl group and Y is a chloro or bromo atom. Thus, the stereoselective heterogeneous hydrogenation of the exocyclic methylene group of a compound of formula II, or an acid addition salt thereof or the simultaneous dehalogenation and stereoselective hydrogenation of a compound of formula III, or an acid addition salt thereof, is carried out in the presence of a rhodium salt catalyst, in which the rhodium is bonded via an amine residue to a polysiloxane.

It has further been discovered that the quantity of these heterogeneous catalysts, in terms of rhodium itself, necessary for complete hydrogenation, is drastically less than has been used for the heterogeneous preparations of the prior art. Additionally, the quantity of rhodium is inferior to the amounts used in the prior art homogeneous processes. An additional dramatic advantage, which renders the present invention extremely economic, is that the catalysts can be recovered after use, by simple filtration. The recovered catalysts can then be either re-used, or the rhodium can be recovered by classical chesrical/physical means. Such recoveries in the prior art homogeneous hydrogenations are either not feasible or are low-yielding, difficult, and thus uneconomical, processes.

The compounds of formula I are well-known semi-synthetic antibiotics, used throughout the world for the treatment of numerous infections in humans and in animals. The most important is α-6-deoxy-5-hydroxy-tetracycline, which has X as a hydroxyl group, and which is commonly called doxycycline. The β-epimer, 6-epi-doxycycline, is devoid of clinical interest, so it is extremely important that the hydrogenation does not co-produce this diastereoisomer. In fact, the limit as established in the British Pharmacopoeia 1980 is 2%. Obviously, this requirement implies that (a) purification step(s) must be found, if the isolated product contains more than 2% of the β-epimer.

In the prior art, only heterogeneous catalysis was taught up to 1972, whilst after this date, the preferred method has been homogeneous catalysis.

The preparation and isolation of doxycycline in a pure form was first described in U.S. Pat. No. 3,200,149, applied for in 1960. The catalyst was 5% rhodium-on-carbon, furnishing a 23.9% weight/weight yield, contaminated with an equal amount of the unrequired β-epimer. Pure α-6-deoxy-5-hydroxytetracycline was obtained by counter-current distribution.

In U.S. Pat. No. 3,444,198 (priority 1967), the use of catalyst poisons, such as quinoline-sulphur, with 5% palladium-on-carbon or 5% rhodium-on-carbon, was shown to improve the ratio of α-epimer to β-epimer. However, the yield was still low and the requirement of extensive purification remained, because of the presence of the β-epimer and degradation products.

British Pat. No. 1,360,006 (Portuguese priorities 1970 and 1971) indicated that the use of a mixture of hydrazine and palladium-on-carbon or platinum-on-carbon, without adding hydrogen, gave improved specificity for the α-epimer. However, in this case, the major impurity was 6-demethyl-6-deoxy-6-methylene-5-hydroxy-tetracycline, when the process started from the 11a-chloro-derivative.

In 1973, U.S. Pat. No. 3,954,862 claimed the use of rhodium-on-carbon, plus a phosphine such as triphenylphosphine, and a promoter, such as stannous chloride or hydrochloric acid. The selectivity was much improved, although the yields varied from 40% to 80%.

Later, Hungarian Pat. No. 12042 (priority 1974), as reported in Chemical Abstracts 86, 89476f, (1977) claimed the use of a heterogeneous palladium-on-ultramicroporous active charcoal catalyst. In this case, the quantity of the β-isomer was still outside the 2% limit.

In addition to those, various other patents appeared, such as U.S. Pat. Nos. 3,397,231, 3,795,707 and 4,061,676, which were solely aimed at improved purification techniques. These processes were often long and complicated to perform, demonstrating clearly the poor quality of the products of the then known heterogeneous processes.

All of the above discussed processes are tabulated in Table I, in comparison with the present invention. The advantages of the present invention can be summarised as follows:

1. The stoichiometric yield of pure product, in this case doxycycline, is between 18% and 80% higher than the best prior art processes.

2. The co-production of the undesired β-epimer is minimal, with typically less than 0.2% being formed. This was shown by both circular chromatography as well as by high performance liquid chromatography (hplc), which also showed that no or negligible quantities of starting material or degradation products appeared in the product. In contrast, the product obtained in only five examples in the prior art, passed the 2% limit as laid down in the British Pharmacopoeia. The best of these showed a 0.7% content of the β-epimer, but this was also mixed with 21.2% of starting material and degradation products.

3. The amount of noble metal required for complete reaction was considerably reduced. Thus in the case where the starting material was 6-demethyl-6-deoxy-6-methylene-5-hydroxy-tetracycline, the reduction was between 278 and 9 times, and in the case where the 11a-chloro-analogue was used, the reduction was between 358 and 11 times.

Thus, it can be seen that the present invention provides higher yields of much purer products than the prior art processes, allied with the use of considerably less noble metal. It therefore is an advance on the state of the art in both technical and economic terms.

The first use of a homogeneous catalyst was described in U.S. Pat. No. 4,207,258 (Italian priority 1972), wherein the catalyst was a complex of rhodium with tertiary phosphine, arsine or stibine ligands. U.S. Pat. No. 3,962,331 (Italian priority 1973) extended the above process to the simultaneous reductive dehalogenation of an 11a-halo-6-demethyl-6-deoxy-6-methylene-tetracycline. However, the β-epimer content of the product was still quoted at about 5%. French Pat. No. 2,216,268 (U.S. priority 1973) disclosed the use of the same catalyst, and hplc analysis of a typical reaction mixture indicated a content of 8% of the β-epimer.

Since that time, other patents have appeared such as U.S. Pat. Nos. 3,907,890, 4,001,321 and 3,962,131 all describing variations in the catalytic system and claiming improved stereospecificity.

U.S. patent application Ser. No. 458,067 (Portuguese priority 1982) now U.S. Pat. No. 4,500,458 claimed the use of rhodium-hydrazine-tertiary phosphine homogeneous catalysts. This allowed a dramatic reduction in the quantity of noble metal required for complete hydrogenation, plus the fact that there was almost negligible co-production of the unrequired β-epimer.

Whilst not strictly comparable since the processes are dissimilar, the present invention represents an advance over the prior art homogeneous processes. In Table II, the best examples of the prior art are described. This table shows clearly that the present invention offers the following advantages:

1. Yields and purities are generally superior to the best processes, such as those given in U.S. patent application Ser. No. 458,067.

2. The quantity of catalyst necessary is less than those of U.S. patent application Ser. No. 458,067 and considerably less than any of the other prior art processes.

3. The catalyst of the present invention is easily recoverable by simple filtration, whereas the homogeneous catalysts are either irrecoverable or only recoverable by complicated, expensive and uneconomic procedures. Indeed, in none of the featured patents is a recovery procedure mentioned.

Taking into account the considerable superiority of homogeneous hydrogenation over heterogeneous hydrogenation for the preparation of α-6deoxy-tetracyclines in the prior art, it was absolutely unexpected and surprising that the *heterogeneous* hydrogenation conditions of the present invention were also superior to the prior art homogeneous hydrogenation processes. In fact, the present invention represents the first heterogeneous hydrogenation process to produce α-6-deoxy-tetracyclines, which is effectively stereospecific.

TABLE I

| Patent | Example | Starting Material | Noble Metal | Amount of Noble Metal per g Mot (mg) | Amount of Noble Metal per g ClMot (mg) | Stoichiometric yield of product | Analysis of Product α-epimer | β-epimer | Mot | Decomp. Products | Stoichiometric yield of pure doxycycline |
|---|---|---|---|---|---|---|---|---|---|---|---|
| U.S. Pat. No. 3,200,149 | 32 | Mot | Rh | 50.0 | | 45.8% | 50.0% | 50.0% | | | 22.9% |
| | 33 | Mot HCl | Rh | 27.1 | | 88.0% | 21.8% | 9.4% | 23.5% | NI | 19.2% |
| U.S. Pat. No. 3,444,198 | 20 | Mot pts | Pd | 69.5 | | NI | 48.0% | 7.3% | NI | NI | 48.0% |
| | 24 | ClMot pts | Rh | | 68.1 | 48.5% | 66.7%* | 33.3%* | NI | NI | 32.3%* |
| | 25 | ClMot pts | Rh | | 68.1 | 74.0% | 50.0%* | 50.0%* | NI | NI | 37.0%* |
| | 31 | ClMot pts | Pd | | 68.1 | 62.5% | 48.0% | 5.6% | NI | NI | 30.0% |
| | 32 | ClMot pts | Pd | | 68.1 | 67.1% | 51.8% | 7.0% | NI | NI | 34.8% |
| | 64 | ClMot pts | Pd | | 17.0 | 57.6% | 93.6% | NI | NI | NI | 53.9% |
| | 69 | ClMot pts | Pd | | 17.0 | 68.6% | 78.1% | 0.7% | NI | NI | 53.6% |
| G.B. Patent 1,360,006 | 4 | ClMot HF | Pt | | 52.1 | 57.0% | 53.0% | 4.0% | 41.0% | 2.0% | 30.2% |
| U.S. Pat. No. 3,954,862 | 3 | Mot HCl | Rh | 2.3 | | NI | 81.0%ϕ | 1.6%ϕ | NI | NI | 80.0% |
| | 4 | Mot HCl | Rh | 23.0 | | NI | 80.0%ϕ | 1.5%ϕ | NI | NI | 78.0% |
| | 6 | ClMot pts | Rh | | 20.3 | 71.5% | 55.5% | 1.8% | 2.0% | NI | 39.7% |
| | 17 | ClMot pts | Rh | | 2.1 | 86.7% | 59.9% | 1.33% | 0.8% | NI | 51.9% |
| Hung. Patent 12042 | | | | | | | | | | | |
| Chem. Abs. 86, 89476f, (1977) | | Mot SS | Pd | 12.4 | | 76.5% | 92.0% | 3.0% | 1.0% | NI | 70.4% |
| Present Invention | 1 | Mot HCl | Rh | 0.25 | | 87.4% | 99.6% | 0.2% | 0 | 0.2% | 87.0% |
| | 4 | Mot HCl | Rh | 0.41 | | 99.1% | 99.5% | 0.2% | 0 | 0.3% | 98.6% |
| | 6 | ClMot pts | Rh | | 0.19 | 89.9% | 99.5% | 0.1% | 0 | 0.4% | 89.5% |
| | 10 | Mot HCl | Rh | 0.37 | | 91.4% | 99.5% | 0.2% | 0.1% | 0.2% | 91.0% |
| | 13 | ClMot pts | Rh | | 0.38 | 90.1% | 99.7% | 0.2% | 0 | 0.1% | 89.8% |

Notes
Mot is 6-demethyl-6-deoxy-6-methylene-5-hydroxy-tetracycline
ClMot is 11a-chloro-6-demethyl-6-deoxy-6-methylene-5-hydroxy-tetracycline
HCl is hydrochloric acid
HF is hydrofluoric acid
pts is p-toluenesulphonic acid
SS is 5-sulphosalicylic acid
* - is assuming no decomposition products were present
ϕ - content from analysis of the reaction mixture
NI - not indicated

TABLE II

| Patent | Example | Starting Material | Noble Metal | Amount of Noble Metal per g Mot (mg) | Amount of Noble Metal per g ClMot (mg) | Stoichiometric yield of product | α-epimer | β-epimer | Mot | Decomp. Products | Stoichiometric yield of pure doxycycline |
|---|---|---|---|---|---|---|---|---|---|---|---|
| U.S. Pat. No. 4,207,258 | 1 | Mot HCl | Rh | 26.4 | | NI | 95.0%$^\phi$ | 5.0%$^\phi$ | NI | Traces | 73.2%$^\theta$ |
| | 2 | Mot HCl | Rh | 21.2 | | NI | 95.0%$^\phi$ | 5.0%$^\phi$ | NI | Traces | 74.6%$^\theta$ |
| | 3 | Mot HCl | Rh | 26.4 | | NI | NI | NI | NI | NI | 71.9%$^\theta$ |
| French Patent 2,216,268 | 1 | Mot | Rh | 132.3 | | 85.0% | 92.0%$^\phi$ | 8.0%$^\phi$ | NI | NI | 78.2%$^\phi$ |
| | 2 | Mot | Rh | 132.3 | | 70.0% | 71.0%$^\phi$ | 29.0%$^\phi$ | NI | NI | 49.7%$^\phi$ |
| | 3 | Mot HCl | Rh | 23.0 | | 90.6% | 95.0%$^\phi$ | 0.7%$^\phi$ | NI | NI | 86.0%$^\phi$ |
| | 5 | Mot HCl | Rh | 2.3 | | 89.2% | NI | 0.6% | 0% | NI | NI |
| | 7 | ClMot pts | Rh | | 21.7 | 78.7% | 89.0% | 1.5-2%$^\phi$ | NI | NI | 70.1% |
| | 9 | Mot HCl | Rh | 0.6 | | 78.4%$^\Phi$ | 78.4$^\Phi$ | 0.8%$^\Phi$ | 5.2%$^\Phi$ | NI | 61.5%$^\Phi$ |
| | 14 | ClMot HCl | Rh | | 2.2 | 81.2% | 88.29% | NI | NI | NI | 71.7% |
| U.S. Pat. No. 3,962,331 | 1 | ClMot pts | Rh | | 4.9 | NI | ~95.0%$^\phi$ | ~5.0%$^\phi$ | NI | Slight Traces | 69.4%$^\theta$ |
| | 2 | ClMot pts | Rh | | 2.7 | NI | NI | NI | NI | NI | 68.7%$^\theta$ |
| U.S. Pat. No. 3,907,890 | 5 | Mot HCl | Co | 268.6 | | 75.2% | 98.0% | 2.0% | NI | NI | 73.7% |
| U.S. Pat. No. 4,001,321 | 1 | Mot HCl | Rh | 10.1 | | 94.7% | 93.0%$^\theta$ | 2-3%$^\phi$ | NI | NI | 88.1% |
| U.S. Pat. No. 3,962,131 | 2 | Mot HCl | Rh | 3.6 | | 98.6% | 99.7%$^\theta$ | NI | NI | NI | 98.4% |
| U.S. Pat. No. Application Ser. No. 458,067 | 2 | Mot HCl | Rh | 0.37 | | 90.2% | 99.5% | 0.45% | Traces | 0 | 89.7% |
| | 3A | ClMot pts | Rh | | 0.35 | 84.2% | 99.8% | 0% | 0 | Slight traces | 84.0% |
| | 4 | Mot HCl | Rh | 0.67 | | 99.1% | 99.89% | 0% | 0 | Slight traces | 99.0% |
| | 13 | ClMot pts | Rh | | 0.38 | 90.7% | 99.6% | 0.3% | 0 traces | Slight | 90.3% |
| | 16 | ClMot pts | Rh | | 0.22 | 85.9% | 99.65% | 0% | Traces | Slight traces | 85.6% |
| Present Invention | 1 | Mot HCl | Rh | 0.25 | | 87.4% | 99.6% | 0.2% | 0 | 0.2% | 87.0% |
| | 4 | Mot HCl | Rh | 0.41 | | 99.1% | 99.5% | 0.2% | 0% | 0.3% | 98.6% |
| | 6 | ClMot pts | Rh | | 0.19 | 89.9% | 99.5% | 0.1% | 0 | 0.4% | 89.5% |
| | 10 | Mot HCl | Rh | 0.37 | | 91.4% | 99.5% | 0.2% | 0.1% | 0.2% | 91.0% |
| | 13 | ClMot pts | Rh | | 0.38 | 90.1% | 99.7% | 0.2% | 0 | 0.1% | 89.8% |

Notes
Mot is 6-demethyl-6-deoxy-6-methylene-5-hydroxy-tetracycline
ClMot is 11a-chloro-6-demethyl-6-deoxy-6-methylene-5-hydroxy-tetracycline
HCl is hydrochloric acid
pts is p-toluenesulphonic acid
$\phi$ - content from analysis of the reaction mixture
$\Phi$ - based upon both fractions obtained
$\theta$ - content from U.V. analysis
NI - not indicated Thus, the present invention allows the production of doxycycline in extremely high yields and purity, and the easy recovery of the noble metal provides extremely important economic advantages over the prior art.

The present invention applies to the stereospecific hydrogenation of the exocyclic 6-methylene group of compounds of formula II, and the simultaneous reductive dehalogenation and stereoselective hydrogenation of the exocyclic 6-methylene group of compounds of formula III.

<chemical structure of formula (II): tetracycline derivative with CH₂, X, N(CH₃)₂, OH, CONH₂, OH groups>

<chemical structure of formula (III): tetracycline derivative with CH₂, X, N(CH₃)₂, OH, CONH₂, OH, Y groups>

This hydrogenation can be carried out in a traditionally designed stainless steel hydrogenator. The reaction temperature of the hydrogenation is preferably between 50° C. and 100° C., preferentially between 60° C. and 90° C. The reaction is too slow at temperatures below 50° C. and deecomposition of both starting material and product occurs above 100° C. The pressure of hydrogen used in the reaction is preferably between 0.1 kg/cm$^2$, and 20 kg/cm$^2$, preferentially between 4 kg/cm$^2$ and 10 kg/cm$^2$.

The starting materials can be prepared according to any of the processes in the prior art, on the condition that no catalyst poison is present in the product so prepared. Starting materials of formula II, for example methacycline, can be advantageously prepared according to the process in British Pat. No. 1,360,006, which also describes a synthesis of a preferred starting material of formula III, 11a-chloro-methacycline.

The catalysts can be prepared according to European Patent Application No. 82106356.7 (Pub. No. 0072435), and are available commercially. The formulae of the catalysts are:

Catalyst A—RhCl$_3$[N{(CH$_2$)$_3$ SiO$_{3/2}$}$_3$]$_{10}$

Catalyst B—RhCl$_3$[N{(CH$_2$)$_3$ SiO$_{3/2}$}$_3$]$_{12}$

Catalyst C—RhCl$_3$[N{(CH$_2$)$_3$ SiO$_{3/2}$}$_3$ ]$_{15}$

Catalyst D—RhCl$_3$[HN{(CH$_2$)$_3$ SiO$_{3/2}$}$_2$ ]$_4$

Catalyst E—RhCl$_3$[HN{(CH$_2$)$_3$ SiO$_{3/2}$}$_2$ ]$_8$ although being polymeric, these are the formulae which best fit the found elemental contents. The quantity of catalyst, and thus of rhodium, forms an important inventive step of the present invention, in that it is considerably less than the quantities typically used in the prior art. Preferably, the rhodium is present in between 0.1 and 5 mmoles per mole of the 6-methylene substrate.

In the case where the starting material is of formula II, such as, for example, methacycline, the reaction is carried out in the presence of a tertiary phosphine, of the following formula:

wherein R$_1$ and R$_2$ are phenyl, substituted phenyl or dimethylamino groups and R$_3$ is a phenyl, substituted phenyl, alkyl, aralkyl, benzyl or dimethylamino group. The preferred tertiary phosphine is triphenylphosphine.

The quantity of the tertiary phosphine is an important variable. As can be seen from Example 8, wherein a less than equimolar amount of the tertiary phosphine was used in comparison with the 11a-chloro starting material, the reaction had not gone to completion after 6 hours 30 minutes, but had after 8 hours in Example 9. In Examples 6 and 7, the tertiary phosphine was present in slightly above equimolar amount and in both cases the hydrogenations were complete in 6 hours 30 minutes. Further in Example 2, there was no reaction when no tertiary phosphine was present. However, addition of a small amount of such a tertiary phosphine allowed complete reaction. Thus, it can be seen that the tertiary phosphine promotes the hydrogenation reaction. However, the quantity of the tertiary phosphine promoter must be carefully controlled, since in larger amounts it enters into competitive reaction, causing slower reaction rates. The optimum amount can be found by routine experimentation for each individual case.

In the case where the starting material is of formula III, such as, for example, 11a-chloro-methacycline, the tertiary phosphine, as defined above, should at least be present in about an equimolar amount with respect to the tetracycline starting material. Any excess over this equimolar amount should be carefully controlled, as for the previous case. Again, routine experimentation will soon allow accurate determination of the optimum amount.

It has been found that the pH of the reaction mixture has an influence on the course of the reaction. Thus addition of minute quantities of, for instance, concentrated hydrochloric acid or 40% aqueous hydrofluoric acid, in the region of 0.05 to 0.50% volume/volume based upon the quantity of solvent present, causes increased yields with reduced reaction times.

The reaction solvent should be inert in the reaction, by which is meant that it should not effect the course of the reaction unfavourably. Hence, the preferred group of such solvents is the lower alcohols, wherein there is between 1 and 6 carbon atoms. The most preferred solvent is methanol.

The reaction time is dependent on many factors, such as reaction temperature, amount of catalyst and type of hydrogenator. A satisfactory reaction time is from about 3 hours to about 10 hours, although equally good results can be obtained after longer reaction times, such as up to 16 hours.

The hydrogenation is stopped when the rate of consumption of hydrogen decreases dramatically. The reaction mixture, at this stage, usually contains no, or negligible amounts of starting material. Similarly, the amount of by-products or decomposition products is negligible, whilst the content of the unrequired $\beta$-epimer is typically less than 0.2%, usually between 0 and 0.1%.

The fact that the reaction mixture virtually contains only the required $\alpha$-epimer, allows the product to be crystallised directly by the addition of p-toluenesulphonic acid. Obviously, this p-toluenesulphonic acid salt should not be soluble in the chosen reaction solvent. In the case of preparation of doxycycline p-toluenesulphonate, the solvent is preferably methanol.

The doxycycline p-toluenesulphonate so obtained can be transformed into other doxycycline salts and complexes by standard methods well known to those skilled in the art. The transformation into doxycycline hydrochloride hemihydrate hemiethanolate (doxycycline hyclate) can be accomplished in one step in an almost quantitative yield, the product complying with the monographs of the internationally recognised pharmacopoeias without any necessity for purification.

From the herein discussed advantages over the prior art, the practical ease with which the present invention can be used, clearly demonstrate the unexpected superiority of the chloro-rhodium-(aminopolysiloxane) catalysts.

The following Examples serve to illustrate the present invention, without in any way limiting the scope thereof.

EXAMPLE 1

Catalyst A (50.0 mg; 3.47% rhodium) in methanol (20 ml) was added to a conventional stainlass steel hydrogenator, which contained 6-demethyl-6-deoxy-6-methylene-5-hydroxy-tetracycline hydrochloride (7.35 g; 15.35 mmoles) and triphenylphosphine (100.0 mg; 0.38 mmoles) in methanol (40 ml), under magnetic stirring. After purging with nitrogen, hydrogen was added to a pressure of 8.0 kg/cm$^2$, and the mixture was then heated to 88° C. After 6 hours 30 minutes, the rate of consumption of hydrogen was effectively zero, and the mixture was cooled to room temperature. The reaction mixture was filtered through a G4 sintered glass filter and the filtered solid recovered and dried. To the filtrate was added p-toluenesulphonic acid (3.30 g; 17.35 mmoles) with stirring. The crystals of $\alpha$-6-deoxy-5-hydroxy-tetracycline p-toluenesulphonate were collected by filtration, washed with acetone (2×10 ml) and dried at 35° C., and yielded 8.27 g. The product was analysed by hplc (column: Machery-Nagel Cat. No. 715382; solvent system: tetrahydrofuran (690 ml), dimethylformamide (110 ml), acetic acid (160 ml), bi-distilled water (40 ml), disodium ethylenediaminetetraacetic acid (15 mg) controlled to a pH of 3.65; flow rate: 1.5 ml; column temperature: 40 C; detection: by U.V. at 268 nm), which indicated the content of the $\alpha$-epimer to be 99.6%, that of the $\beta$-epimer to be 0.2%, that of starting material to be zero, and that of an unidentified impurity to be 0.2%. Thus, the stoichiometric yield of the product "as it is" was 87.4% and of the pure doxycycline p-toluenesulphonate was 87.0%

EXAMPLE 2

The conditions of Example 1 were repeated, except for the quantity of Catalyst A (92.0 mg; 3.02% rhodium) used and that the triphenylphosphine was omitted.

There was no consumption of hydrogen and the starting material was recovered unchanged.

EXAMPLE 3

The conditions of Example 1 were repeated except that the quantities of Catalyst A (80.0 mg; 3.47% rhodium) and triphenylphosphine (50.0 mg; 0.19 mmoles) were slightly altered.

The product, doxycycline p-toluenesulphonate, weighed 8.40 g, and gave by hplc assay 99.7% α-epimer, 0.1% β-epimer, 0.1% starting material and the rest being divided between two unidentified impurities. The stoichiometric yield of pure product was thus 88.5%.

EXAMPLE 4

Catalyst A (92.5 mg; 3.00% rhodium) in methanol (20 ml) was added to a conventional stainless steel hydrogenator, which contained 6-demethyl-6-deoxy-6-methylene-5-hydroxy-tetracycline hydrochloride (7.32 g; 15.29 mmoles), triphenylphosphine (25.0 mg; 0.10 mmoles) and concentrated hydrochloric acid (10 μl) in methanol (40 ml), under magnetic stirring. After purging with nitrogen, hydrogen was added to a pressure of 8.0 kg/cm$^2$, and the mixture was then heated to 88° C. After 5 hours 30 minutes, the rate of consumption of hydrogen was effectively zero, and the mixture was cooled to room temperature. The reaction mixture was filtered through a G4 sintered glass filter and the filtered solid recovered and dried. To the filtrate was added p-toluenesulphonic acid (3.30 g; 19.16 mmoles) with stirring. The crystals of α-6-deoxy-5-hydroxy-tetracycline p-toluenesulphonate were collected by filtration, washed with acetone (2×10 ml) and dried at 35° C., and yielded 9.34 g. The product was analysed by hplc, which indicated the content of the α-epimer to be 99.5%, that of the β-epimer to be 0.2%, that of starting material to be zero, and that of an unidentified impurity to be 0.3%. Thus, the stoichiometric yield of the product "as it is" was 99.1% and of the pure doxycycline p-toluenesulphonate was 98.6%

Doxycycline p-toluenesulphonate (40.0 g) prepared according to the process above was suspended in a mixture of ethanol (72.0 ml) and water (24.0 ml), with stirring. A solution of triethylamine (9.04 ml) in ethanol (9.04 ml) was added, causing dissolution followed by crystallisation. After stirring for 20 minutes, ethanol (144 ml) was added and the mixture stirred for a further 1 hour 30 minutes. The crystals were filtered, washed with ethanol (25 ml), then with acetone (12.5 ml) and dried at 35° C. The product, doxycycline monohydrate, weighed 22.12 g and complied with the U.S. Pharmacopoeia monograph requirements. The mother liquors were diluted with an equal volume of water and 5-sulphosalicylic acid (2.0 g) was added. After stirring overnight, the deposited solid was filtered, washed with 66% aqueous methanol and then with acetone, dried at 35° C., and gave 1.53 g of doxycycline sulphosalicylate.

The doxycycline monohydrate (5.0 g) prepared as above was dissolved in a mixture of ethanol (5 ml), water (2.5 ml) and concentrated hydrochloric acid (1.08 ml). The mixture was filtered through a cellulose filter aid, and ethanol containing 18% hydrogen chloride (10 ml) and concentrated hydrochloric acid (2.5 ml) were added to the clear filtrate. The mixture was stirred for 2 hours, during which time doxycycline hyclate crystallised. The crystals were filtered, washed with ethanol (6.0 ml), then with acetone (3.0 ml), and dried at 35° C., and yielded 5.06 g. The product complied with all of the requirements of the respective monographs in the British Pharmacopoeia 1980 and the U.S. Pharmacopoeia XX.

EXAMPLE 5

The conditions of Example 4 were repeated substituting the concentrated hydrochloric acid for 40% aqueous hydrofluoric acid. The yield of doxycycline p-toluenesulphonate was 8.56 g. Hplc analysis showed that the α-epimer content was 99.7% and the β-epimer content was 0.2%, indicating that the pure stoichiometric yield was 90.5%.

EXAMPLE 6

To a conventional stainless steel hydrogenator containing 11a-chloro-6-demethyl-6-deoxy-6-methylene-5-hydroxy-tetracycline p-toluenesulphonate (20.00 g; 30.81 mmoles) and triphenylphosphine (8.10 g; 30.88 mmoles) in methanol (105 ml), was added, with stirring, a suspension of Catalyst A (92.0 mg; 3.02% rhodium) in methanol (15 ml). After purging with nitrogen, the hydrogenator was heated to 88°-9° C. and filled with hydrogen to a pressure of 8 kg/cm$^2$. After 7 hours 30 minutes, the reaction mixture was cooled to about 45° C., and p-toluenesulphonic acid (6.60 g; 34.70 mmoles) was added. The mixture was stirred for 2 hours, whilst being cooled to 0° C. The crystals so formed were filtered, washed with methanol (2×5.5 ml) and then acetone (2×5.5 ml), dried at 35°-40° C. to yield 17.09 g. Hplc assay indicated that the α-epimer content was 99.5%, whilst the β-epimer content was 0.1%.

Doxycycline p-toluenesulphonate (35.0 g) prepared as above was dissolved in a mixture of acetone (105 ml) and concentrated hydrochloric acid (16.45 ml). The solution was then filtered, and the recovered solid dried. Ethanol (35 ml) was added to the clear filtrate, and the mixture was stirred at room temperature for 2 hours 30 minutes. The crystals thus formed were filtered, washed with ethanol (41.5 ml) and then with acetone (20.75 ml), dried at 35° C. and gave 23.3 g of doxycycline hyclate. This product was indistinguishable from that obtained according to Example 4, complying in all aspects with the respective monographs in the British Pharmacopoeia 1980 and the U.S. Pharmacopoeia XX. The mother liquors were diluted with an equal volume of water and 5-sulphosalicylic acid (5.25 g) was added. After stirring overnight and recovery in the usual manner, the product, doxycycline sulphosalicylate, weighed 5.96 g.

EXAMPLE 7

In a conventional stainless steel hydrogenator were mixed 11a-chloro-6-demethyl-6-deoxy-6-methylene-5-hydroxy-tetracycline p-toluenesulphonate (10.00 g; 15.41 mmoles), and triphenylphosphine (4.10 g; 15.63 mmoles) in methanol (40 ml), to which was added a suspension of Catalyst A (40.0 mg; 3.47% rhodium) in methanol (20 ml). The hydrogenation was carried out at 88° C. for 6 hours 30 minutes, after which the reaction mixture was filtered and p-toluenesulphonic acid (3.30 g; 17.35 mmoles) was added. The doxycycline p-toluenesulphonate which crystallised, was filtered, washed with acetone (2×10 ml), dried at 35° C., and yielded 8.32 g. Hplc analysis showed that it contained 99.8% α-epimer and less than 0.1% β-epimer, indicating a stoichiometric yield of pure product of 87.4%.

EXAMPLE 8

The conditions of Example 7 were repeated except that the quantities of Catalyst A (46.0 mg; 3.02% rhodium) and triphenylphosphine (4.00 g; 15.25 mmoles) were slightly altered. Thus, the quantity of triphenylphosphine was less than equimolar with respect to the quantity of the starting material. Isolation of the product in the normal fashion gave 7.37 g, which was shown by circular chromatography (paper: Schleicher & Schüll, 265 mm diameter, reference 2045B; stationary phase: 0.1M citric acid (100 ml) and 0.2M anhydrous disodium phosphate (40 ml) were mixed to give a buffer with pH 3.5; mobile phase: nitromethane:chloroform:pyridine- 20:10:3) to contain α-6-deoxy-5-hydroxy-tetracycline, plus about 5% of 6-demethyl-6-deoxy-6-methylene-5-hydroxy-tetracycline. No β-epimer was detectable at all.

EXAMPLE 9

The conditions of Example 8 were repeated, except that the hydrogenation was continued for 8 hours. The yield of doxycycline p-toluenesulphonate was 7.83 g, and by circular chromatography the product contained only the required α-epimer. Hplc confirmed the above, indicating the β-epimer to be 0.2%.

EXAMPLE 10

Catalyst B (120.0 mg; 2.08% rhodium) in methanol (20 ml) was added to a conventional stainless steel hydrogenator, which contained 6-demethyl-6-deoxy-6-methylene-5-hydroxy-tetracycline hydrochloride (7.38 g; 15.41 mmoles), concentrated hydrochloric acid (10 µl) and triphenylphosphine (50.0 mg; 0.19 mmoles) in methanol (40 ml), under magnetic stirring. After purging with nitrogen, hydrogen was added to a pressure of 8.0 kg/cm$^2$, and the mixture was then heated to 88° C. After 6 hours, the rate of consumption of hydrogen was effectively zero, and the mixture was cooled to room temperature. The reaction mixture was filtered through a G4 sintered glass filter and the filtered solid recovered and dried. To the filtrate was added p-toluenesulphonic acid (3.30 g; 17.35 mmoles) with stirring. The crystals of α-6-deoxy-5-hydroxy-tetracycline p-toluenesulphonate were collected by filtration, washed with acetone (2×10 ml) and dried at 35° C., and yielded 8.69 g. The product was analysed by hplc, which indicated the content of the α-epimer to be 99.5% and that of the β-epimer to be 0.2%. Thus, the stoichiometric yield of the product "as it is" was 91.4% and of the pure doxycycline p-toluenesulphonate was 91.0%

EXAMPLE 11

The conditions of Example 10 were repeated with Catalyst D (33.0 mg; 8.37% rhodium), but omitting hydrochloric acid. The doxycycline p-toluenesulphonate obtained in the usual fashion weighed 8.58 g, which corresponds to a 90.3% stoichiometric yield. Hplc analysis indicated that the product contained 99.9% α-epimer and 0.1% β-epimer. No starting material or decomposition products were detectable.

EXAMPLE 12

In a conventional stainless steel hydrogenator were mixed lla-chloro-6-demethyl-6-deoxy-6-methylene-5-hydroxy-tetracycline p-toluenesulphonate (10.00 g; 15.41 mmoles), 40% aqueous hydrofluoric acid (10 µl) and triphenylphosphine (4.10 g; 15.63 mmoles) in methanol (40 ml), and a suspension of Catalyst C (80.0 mg; 2.42% rhodium) in methanol (20 ml) was added. The hydrogenation was carried out at 88° C. for 6 hours, after which the reaction mixture was filtered and p-toluenesulphonic acid (3.30 g; 17.35 mmoles) was added. The doxycycline p-toluenesulphonate which crystallised, was filtered, washed with acetone (2×5 ml), dried at 35° C., and yielded 8.40 g. Hplc analysis showed that it contained 99.6% α-epimer and about 0.2% β-epimer, indicating a stoichiometric yield of pure product of 88.1%.

EXAMPLE 13

In a conventional stainless steel hydrogenator were mixed lla-chloro-6-demethyl-6-deoxy-6-methylene-5-hydroxy-tetracycline p-toluenesulphonate (10.00 g; 15.41 mmoles) and triphenylphosphine (4.05 g; 15.44 mmoles) in methanol (40 ml), to which was added a suspension of Catalyst E (56.0 mg; 4.94% rhodium) in methanol (20 ml). The hydrogenation was carried out at 88° C. for 6 hours, after which the reaction mixture was filtered and p-toluenesulphonic acid (3.30 g; 17.35 mmoles) was added. The doxycycline p-toluenesulphonate which crystallised, was filtered, washed with acetone (2×5 ml), dried at 35° C., and yielded 8.56 g. The product contained 99.7% α-epimer by hplc analysis, which represents a stoichiometric yield of 89.8%.

I claim:

1. A process for the preparation of α-6-deoxy-tetracyclines by the stereoselective heterogeneous hydrogenation of a 6-demethyl-6-deoxy-6-methylene-tetracycline or an acid addition salt thereof, in the presence of a tertiary phosphine, or the simultaneous dehalogenation and stereoselective hydrogenation of an lla-halo-6-demethyl-6-deoxy-6-methylene-tetracycline or an acid addition salt thereof, in the presence of a tertiary phosphine, characterised by the use of a rhodium salt catalyst, wherein the rhodium is bonded to an aminopolysiloxane.

2. A process according to claim 1, wherein the product is obtained directly from the reaction mixture as a p-toluenesulphonate salt.

3. A process according to claim 1, wherein the tertiary phosphine is of the formula:

wherein r$_1$ and R$_2$ are phenyl, substituted phenyl or dimethylamino groups, and R$_3$ is a phenyl, substituted phenyl, alkyl, aralkyl, benzyl or dimethylamino group.

4. A process according to claim 3, wherein the tertiary phosphine is triphenylphosphine.

5. A process according to claim 1, wherein the rhodium necessary for complete reaction is present in between 0.1 and 5 mmoles per mole of the 6-methylene-substrate.

6. A process according to claim 1, wherein the rhodium salt catalyst is bonded through a nitrogen containing group to a polysiloxane and has the following formulae:

$$RhCl_3[N\{(CH_2)_3SiO_{3/2}\}_3]_{10}$$

$$RhCl_3[N\{(Ch_2)_3SiO_{3/2}\}_3]_{12}$$

$$RhCl_3[N\{(CH_2)_3SiO_{3/2}\}_3]_{15}$$

$$RhCl_3[HN\{(CH_2)_3SiO_{3/2}\}_2]_4$$

$$RhCl_3[HN\{(CH_2)_3SiO_{3/2}\}_2]_8$$

7. A process according to any one of claims 1–6 wherein the hydrogenation is carried out at a pressure comprised between 0.1 kg/cm$^2$ and 20 kg/cm$^2$ and at a temperature between 50° C. and 100° C., and the reaction medium is a solvent which does not unfavourably effect the course of the hydrogenation.

8. A process according to claim 1 effected in the presence of a reaction inert solvent and 0.05 to 0.50% volume/volume based on solvent of hydrochloric or hydrofluoric acid.

9. A process according to claim 8 wherein the hydrogenation is carried out at a pressure of 0.1–20 kg/cm$^2$ and a temperature of 50°–100° C. and the solvent is a lower alcohol.

10. A process according to claim 9 wherein the pressure is 4–10 kg/cm$^2$, the temperature is 60°–90° C., the phosphine is triphenylphosphine, and the catalyst contains 0.1–5 mmoles of rhodium per mole of 6-methylene tetracycline hydrogenated.

11. A process according to claim 10 wherein the catalyst is of the formula $RhCl_3[N\{(CH_2)_3SiO_{3/2}\}_3]_a$ or $RhCl_3[HN\{(CH_2)_3SiO_{3/2}\}_2]_b$ where a is 10, 12 or 15 and b is 4 or 8.

12. A process according to claim 1 wherein the pressure is 4–10 kg/cm$^2$, the temperature is 60°–90° C., the phosphine is triphenylphosphine, and the catalyst contains 0.1–5 mmoles of rhodium per mole of 6-methylene tetracycline hydrogenated.

13. A process according to claim 12 wherein the catalyst is of the formula $RhCl_3[N\{(CH_2)_3SiO_{3/2}\}_3]a$ or $RhCl_3[HN\{(CH_2)_3SiO_{3/2}\}_2]b$ where a is 10, 12, or 15 and b is 4 or 8.

* * * * *